(12) United States Patent
Johnston et al.

(10) Patent No.: US 8,332,766 B2
(45) Date of Patent: Dec. 11, 2012

(54) METHODS AND SYSTEMS FOR PREVENTING UNAUTHORIZED ACCESS TO PATIENT INFORMATION

(75) Inventors: Jacob Johnston, Winnetka, CA (US); Guillermo A. Calle, Moorpark, CA (US); Fernando Chapa, Harold, CA (US)

(73) Assignee: Advanced Bionics, LLC, Valencia, CA (US)

( * ) Notice: Subject to any disclaimer, the term of this patent is extended or adjusted under 35 U.S.C. 154(b) by 567 days.

(21) Appl. No.: 12/567,011

(22) Filed: Sep. 25, 2009

(65) Prior Publication Data

US 2011/0078595 A1    Mar. 31, 2011

(51) Int. Cl.
*G06F 3/048* (2006.01)
*G06F 7/00* (2006.01)
*G06F 7/04* (2006.01)

(52) U.S. Cl. ........ 715/764; 715/816; 707/722; 707/736; 707/754; 726/26

(58) Field of Classification Search .................. 715/764, 715/816; 707/722, 736, 754; 726/26
See application file for complete search history.

(56) References Cited

U.S. PATENT DOCUMENTS

| | | | |
|---|---|---|---|
| 5,758,095 A | | 5/1998 | Albaum et al. |
| 6,108,665 A | * | 8/2000 | Bair et al. ............................. 1/1 |
| 2004/0153336 A1 | | 8/2004 | Virdee et al. |
| 2004/0204965 A1 | * | 10/2004 | Gueck et al. ....................... 705/3 |
| 2008/0103798 A1 | * | 5/2008 | Domenikos et al. .............. 705/1 |
| 2010/0241844 A1 | * | 9/2010 | Hussain et al. ............... 713/150 |

FOREIGN PATENT DOCUMENTS

WO    WO-2008/022758    2/2008

OTHER PUBLICATIONS

International Search Report and Written Opinion received in International Application No. PCT/US2010/049547 dated Mar. 22, 2011.

* cited by examiner

*Primary Examiner* — Ting Lee
(74) *Attorney, Agent, or Firm* — AdvantEdge Law Group, LLC (57) ABSTRACT

An exemplary method includes displaying a graphical user interface configured to include a patient list displayed therein, receiving user input representative of a search term comprising one or more characters selected to identify a particular patient included within a plurality of patients, dynamically updating the patient list in response to the received user input to only include a plurality of entries that contain the search term, each of the entries comprising patient information associated with a distinct one of the patients, and preventing one or more non-search term characters contained within each of the entries of the patient list from being displayed within the graphical user interface. Corresponding methods and systems are also disclosed.

17 Claims, 10 Drawing Sheets

| First Name | Last Name | Gender | Birth Date |
|---|---|---|---|
| | Br | | |
| **** | Br*** | Male | 7/23/1975 |
| ******* | Br*** | Female | 6/4/1963 |
| ********* | Br*** | Female | 6/6/1993 |

| First Name | Last Name | Gender | Birth Date |
|---|---|---|---|
|  |  |  |  |
| Jon | Ableton | Male | 4/23/1982 |
| Alyssa | Artimus | Female | 5/30/1998 |
| Christopher | Blansky | Male | 9/12/2004 |
| Mike | Brown | Male | 7/23/1975 |
| Sharron | Brown | Female | 6/4/1963 |
| Elizabeth | Brown | Female | 6/6/1993 |
| Jerry | Bryant | Male | 5/9/1986 |
| Jessica | Cape | Female | 3/21/2007 |
| Brian | Caldwell | Male | 11/16/2001 |
| Mary | Card | Female | 2/28/1950 |
| Richard | Craig | Male | 1/30/1958 |

METHODS AND SYSTEMS FOR PREVENTING UNAUTHORIZED ACCESS TO PATIENT INFORMATION

BACKGROUND

The Health Insurance Portability and Accountability Act ("HIPAA") provides federal protections for personal medical information held by covered entities and gives patients an array of rights with respect to that information. For example, HIPAA requires that appropriate administrative, technical and physical safeguards must be in place to protect the privacy of patient information (e.g., medical records, patient names, social security numbers, etc.). For example, a medical facility, such as a doctor's office or clinic, must ensure that only authorized personnel have access to electronic data representative of patient information.

However, when a medical software application has access to a number of patient files, it will often display a list of patient names on a display screen from which an authorized user (e.g., a hospital staff member) may select a particular patient's name to access patient information corresponding to the patient. However, if the patient happens to be looking at the display screen while the authorized user accesses the patient information, the patient may see the list of patient names. If this happens, HIPAA laws are violated.

SUMMARY

An exemplary method includes displaying a graphical user interface configured to include a patient list displayed therein, receiving user input representative of a search term comprising one or more characters selected to identify a particular patient included within a plurality of patients, dynamically updating the patient list in response to the received user input to only include a plurality of entries that contain the search term, each of the entries comprising patient information associated with a distinct one of the patients, and preventing one or more non-search term characters contained within each of the entries of the patient list from being displayed within the graphical user interface.

Another exemplary method includes maintaining data representative of patient information corresponding to a plurality of patients, receiving user input representative of a search term comprising one or more characters selected to identify a particular patient included within the plurality of patients, dynamically updating a patient list in response to the received user input to only include a plurality of entries that contain the search term, each of the entries comprising patient information associated with a distinct one of the patients, displaying the entries of the patient list within a graphical user interface, and preventing one or more non-search term characters contained within each of the entries of the patient list from being displayed within the graphical user interface.

An exemplary system includes a display facility, a communication facility, and a privacy facility selectively and communicatively coupled to one another. The display facility is configured to display a patient list within a graphical user interface. The a communication facility is configured to receive user input representative of a search term comprising one or more characters selected to identify a particular patient included within a plurality of patients. The privacy facility is configured to dynamically update the patient list in response to the received user input to only include a plurality of entries that contain the search term, each of the entries comprising patient information associated with a distinct one of the patients, and prevent one or more non-search term characters contained within each of the entries of the patient list from being displayed within the graphical user interface.

BRIEF DESCRIPTION OF THE DRAWINGS

The accompanying drawings illustrate various embodiments of the principles described herein and are a part of the specification. The illustrated embodiments are merely examples and do not limit the scope of the disclosure.

Throughout the drawings, identical reference numbers designate similar, but not necessarily identical, elements.

DETAILED DESCRIPTION

Methods and systems for preventing unauthorized access to patient information are described herein. As described in more detail below, a graphical user interface configured to include a patient list displayed therein may be displayed on a display device (e.g., a personal computer screen). A communication facility may receive user input representative of a search term comprising one or more characters selected to identify a particular patient included within a plurality of patients. The patient list may be dynamically updated in response to the received user input to only include a plurality of entries that contain the search term. One or more non-search term characters contained within each of the entries of the patient list may be prevented from being displayed within the graphical user interface. In this manner, as will be described in more detail below, unauthorized access to patient information by a patient or other bystander physically present in the vicinity of the display screen on which the patient list is displayed may be prevented.

As used herein, the term "patient information" refers to any information associated with a particular patient. For example, patient information corresponding to a patient may include, but is not limited to, a name of the patient, a gender of the patient, a birth date of the patient, one or more medical records of the patient, and/or any other medical information associated with the patient as may serve a particular application.

Figure 1:
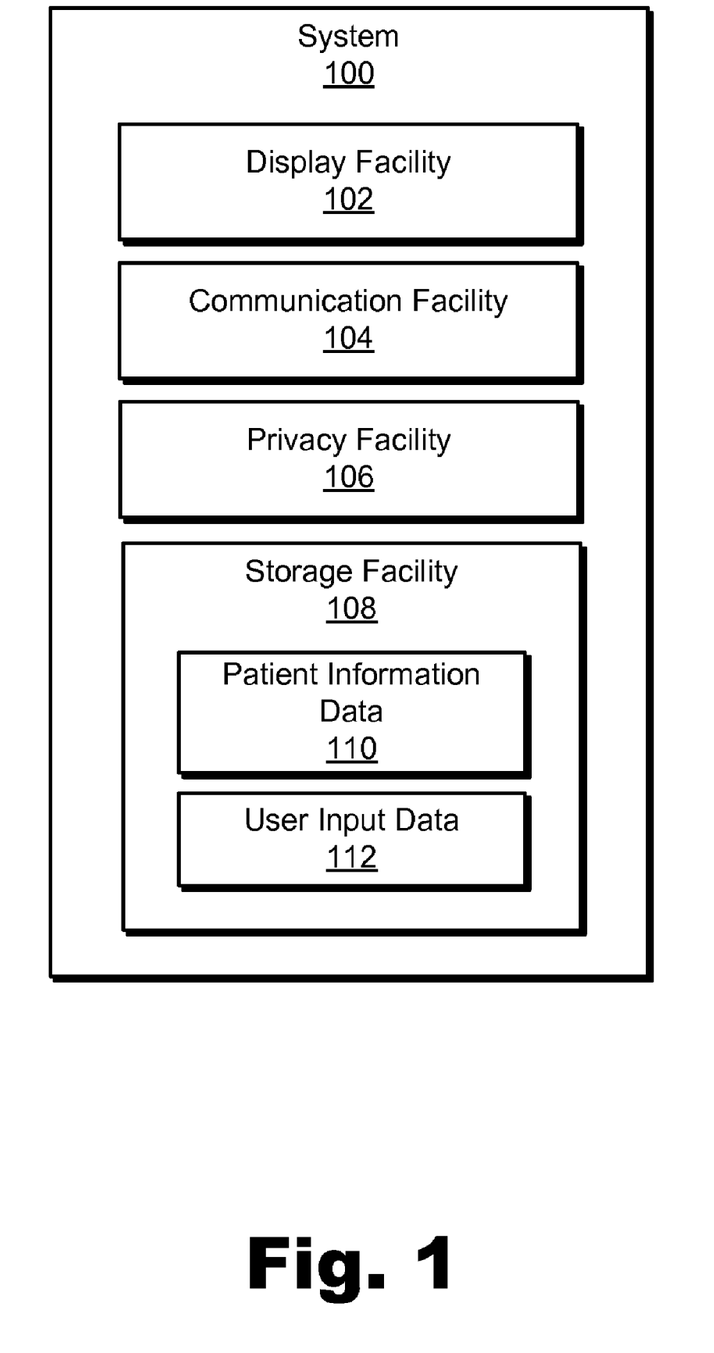
FIG. 1 illustrates an exemplary system for preventing unauthorized access to patient data accessed or used by medical software applications according to principles described herein.

FIG. 1 illustrates an exemplary system 100 for preventing unauthorized access to patient data accessed or used by medical software applications. System 100 may include, but is not limited to, a display facility 102, a communication facility 104, a privacy facility 106, and a storage facility 108 selectively and communicatively coupled one to another.

Display facility 102 may be configured to display a graphical user interface ("GUI") configured to include a patient list displayed therein. As will be described in more detail below, the patient list may be generated by a medical software application and may include one or more entries that each include patient information identifying or otherwise associated with a particular patient. A user may select one of the entries displayed within the patient list to access additional patient information (e.g., medical records) associated with the patient that corresponds to the selected entry.

A medical software application may maintain or access patient information corresponding to multiple patients. Hence, to facilitate access by a user to patient information associated with a particular patient, system 100 may include a communication facility 104 configured to receive user input representative of one or more search terms (also referred to as "filter terms"). The one or more search terms may be input by a user of a medical software application to narrow the patient list until the user can identify and select an entry included within the patient list that corresponds to the particular patient. As will be described in more detail below, each search term input by a user may include a sequence of one or more characters.

Privacy facility 106 may be configured to dynamically update the patient list in response to the user input received by communication facility 104 to only include one or more entries that contain the input search term. As will be described in more detail below, privacy facility 106 may be further configured to prevent one or more non-search term characters contained within each of the entries of the patient list from being displayed within the graphical user interface. For ease of explanation, the term "non-search term characters" will be used herein to refer to characters contained within character sequences included within each of the entries of the patient list that do not match a search term input by a user of a medical software application.

In some examples, privacy facility 106 may be configured to prevent one or more non-search term characters contained within each of the entries of the patient list from being displayed within the graphical user interface by masking or hiding the non-search term characters with password characters. For example, as will be described in more detail below, privacy facility 106 may direct display facility 102 to display a password character in place of one or more non-search term characters contained within each of the entries of the patient list. As used herein, a "password character" may include any character (e.g., the * character) as may serve a particular application.

Additionally or alternatively, privacy facility 106 may be configured to prevent one or more non-search term characters contained within each of the entries of the patient list from being displayed within the graphical user interface by preventing the entire patient list from being displayed within the graphical user interface until the patient list has been narrowed to include only a single entry. In this manner, as will be described in more detail below, the systems and methods described herein may comply with varying privacy policies.

Storage facility 108 may be configured to maintain patient information data 110 and user input data 112. Patient information data 110 may include data representative of patient information corresponding to one or more patients. User input data 112 may include data representative of one or more search terms input by a user.

System 100, including facilities 102-108, may include any computer hardware and/or computer-implemented instructions (e.g., software), or combinations of computer-implemented instructions and hardware, configured to perform one or more of the processes described herein. In particular, system 100 may be implemented on one physical computing device or may be implemented on more than one physical computing device. Accordingly, system 100 may include any number of computing devices, and may employ any of a number of computer operating systems. Moreover, it will be recognized that although facilities 102-108 are shown to be separate facilities in FIG. 1, any of those facilities may be combined into a single facility as may serve a particular application.

Accordingly, one or more of the processes described herein may be implemented at least in part as instructions executable by one or more computing devices. In general, a processor (e.g., a microprocessor) receives instructions, from a computer-readable medium, (e.g., a memory, etc.), and executes those instructions, thereby performing one or more processes, including one or more of the processes described herein. Such instructions may be stored and/or transmitted using any of a variety of known computer-readable media.

A computer-readable medium (also referred to as a processor-readable medium) includes any medium that participates in providing data (e.g., instructions) that may be read by a computer (e.g., by a processor of a computer). Such a medium may take many forms, including, but not limited to, non-volatile media and/or volatile media. Non-volatile media may include, for example, optical or magnetic disks and other persistent memory. Volatile media may include, for example, dynamic random access memory ("DRAM"), which typically constitutes a main memory. Common forms of computer-readable media include, for example, a floppy disk, flexible disk, hard disk, magnetic tape, any other magnetic medium, a CD-ROM, DVD, any other optical medium, a RAM, a PROM, an EPROM, a FLASH-EEPROM, any other memory chip or cartridge, or any other medium from which a computer can read.

Figure 2:
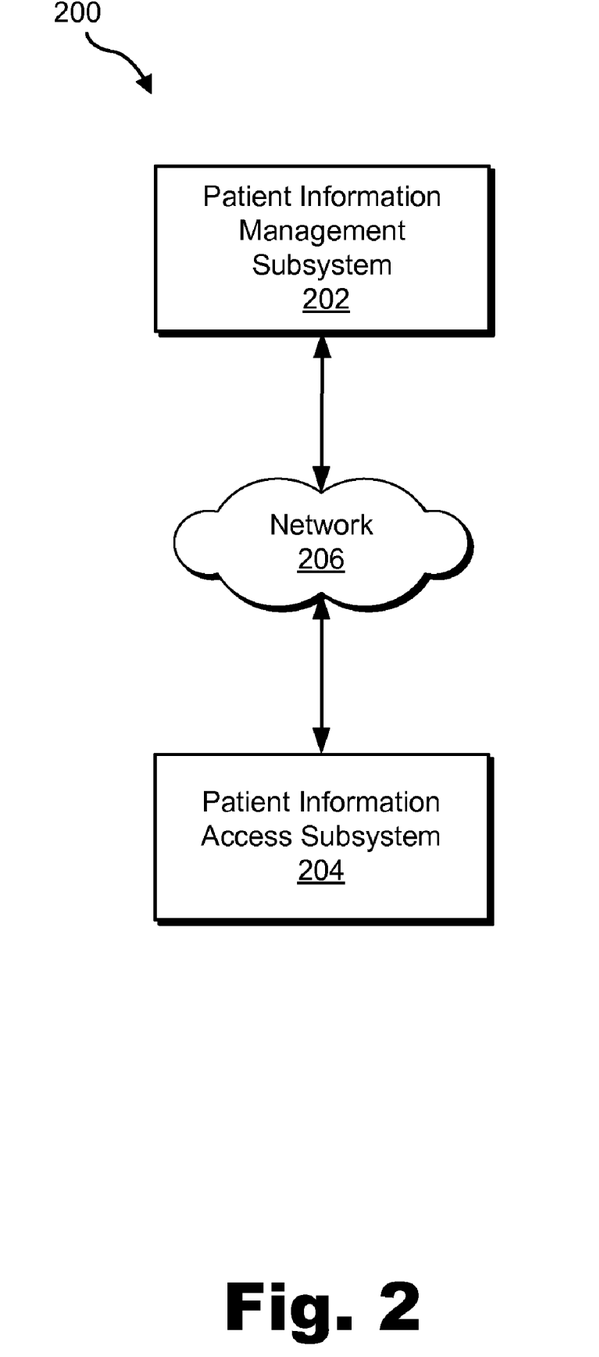
FIG. 2 illustrates an exemplary implementation of the system of FIG. 1 according to principles described herein.

FIG. 2 illustrates an exemplary implementation 200 of system 100 wherein a patient information management subsystem 202 (or simply "management subsystem 202") is communicatively coupled to a patient information access subsystem 204 (or simply "access subsystem 204"). As will be described in more detail below, display facility 102, communication facility 104, privacy facility 106, and/or storage facility 108 may each be implemented on one or both of management subsystem 202 and access subsystem 204.

Access subsystem 204 may be configured to communicate with and receive a signal and/or data stream containing data representative of patient information and/or any other data from management subsystem 202. Access subsystem 204 and management subsystem 202 may communicate using any suitable communication technologies, devices, networks, network platforms, media, and protocols supportive of remote data communications.

For example, as shown in FIG. 2, management subsystem 202 may be configured to communicate with access subsystem 204 over a network 206 (and communications links thereto). Network 206 may include one or more networks or types of networks capable of carrying communications and/or data signals between management subsystem 202 and access subsystem 204. For example, network 206 may include, but is not limited to, a cable network, optical fiber network, hybrid fiber coax network, wireless network (e.g., a Wi-Fi and/or mobile telephone network), satellite network, wireless broadcast network (e.g., a satellite media broadcasting network or terrestrial broadcasting network), subscriber television network, a provider-specific network, the Internet, an intranet, a local area network, any other suitable network, and any combination or sub-combination of these networks.

Management subsystem 202 and access subsystem 204 may communicate over network 206 using any suitable communication technologies, devices, media, and protocols supportive of remote data communications, including, but not limited to, data transmission media, communications devices, Transmission Control Protocol ("TCP"), Internet Protocol ("IP"), File Transfer Protocol ("FTP"), Telnet, Hypertext Transfer Protocol ("HTTP"), Real Time Protocol ("RTP"), User Datagram Protocol ("UDP"), Ethernet, and any other suitable communications technologies, devices, media, and protocols.

While FIG. 2 shows management subsystem 202 and access subsystem 204 communicatively coupled via network 206, it will be recognized that management subsystem 202 and access subsystem 204 may be configured to communicate one with another in any other suitable manner (e.g., via a direct connection).

Figure 3:
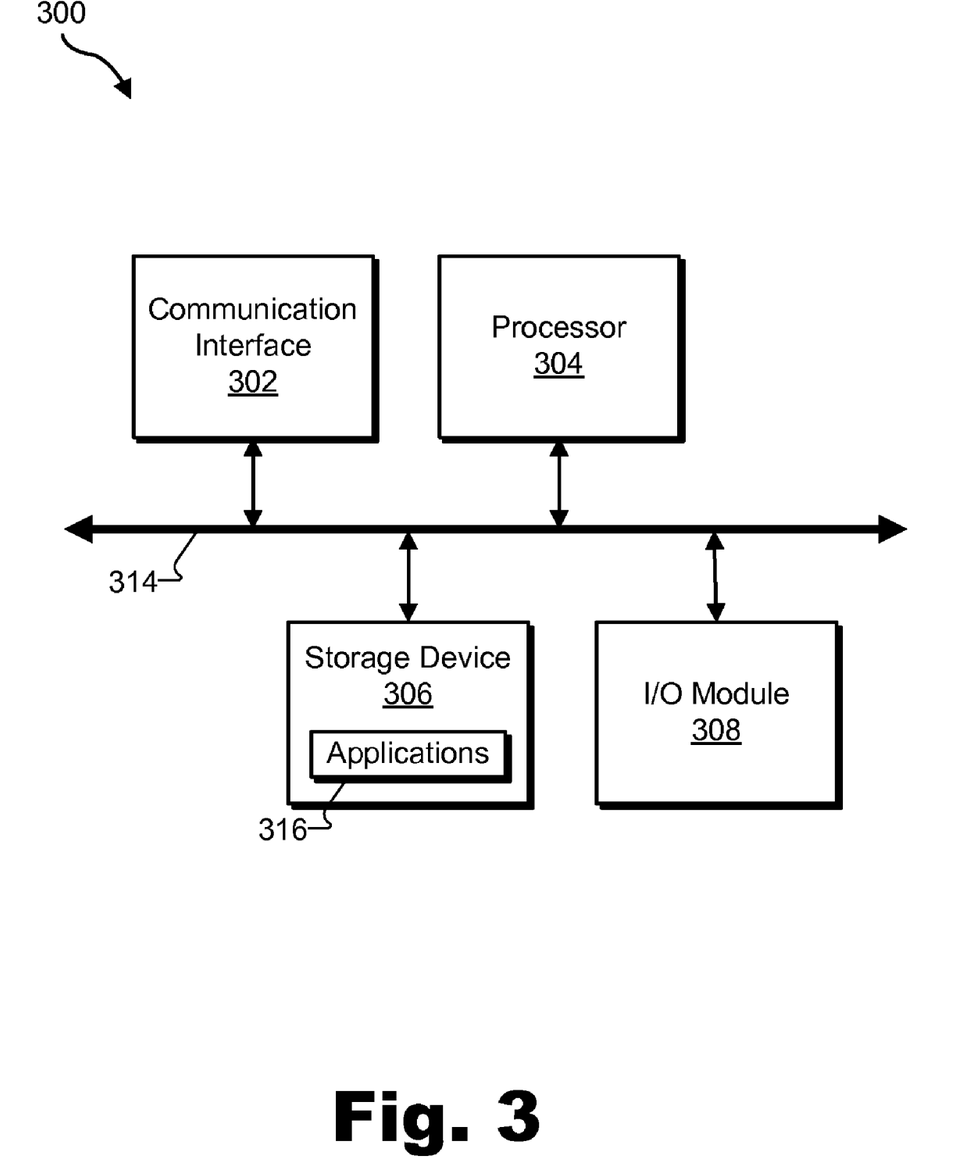
FIG. 3 illustrates an exemplary computing device according to principles described herein.

FIG. 3 illustrates an exemplary computing device 300 that may have any combination of management subsystem 202 and/or access subsystem 204 implemented thereon. Computing device 300 may include one or more of a personal computer, a client device, a server, a mobile device (e.g., a mobile phone device), a handheld device, a phone device, a personal-digital assistant device, a television device, and/or any other computing device configured to perform one or more of the processes and/or operations described herein.

While an exemplary computing device 300 is shown in FIG. 3, the components illustrated in FIG. 3 are not intended to be limiting. Additional or alternative components may be used in other embodiments. Components of computing device 300 shown in FIG. 3 will now be described in additional detail.

Communication interface 302 may be configured to communicate with one or more computing devices. Examples of communication interface 302 include, without limitation, a wired network interface (such as a network interface card), a wireless network interface (such as a wireless network interface card), a modem, and any other suitable interface. In at least one embodiment, communication interface 302 may provide a direct connection between management subsystem 202 and access subsystem 204 via a direct link to a network, such as the Internet. Communication interface 302 may additionally or alternatively provide such a connection through, for example, a local area network (such as an Ethernet network), a personal area network, a telephone or cable network, a cellular telephone connection, a satellite data connection, a dedicated URL, or any other suitable connection. Communication interface 302 may be configured to interface with any suitable communication media, protocols, and formats, including any of those mentioned above.

Processor 304 generally represents any type or form of processing unit capable of processing data or interpreting, executing, and/or directing execution of one or more of the instructions, processes, and/or operations described herein. Processor 304 may direct execution of operations in accordance with one or more applications 316 or other computer-executable instructions such as may be stored in storage device 306 or another computer-readable medium. As an example, processor 304 may be configured to process data representative of a message generated by a software application, including encrypting, decrypting, and/or parsing the data.

Storage device 306 may include one or more data storage media, devices, or configurations and may employ any type, form, and combination of data storage media and/or device. For example, storage device 306 may include, but is not limited to, a hard drive, network drive, flash drive, magnetic disc, optical disc, RAM, DRAM, other non-volatile and/or volatile data storage units, or a combination or sub-combination thereof. Electronic data, including data described herein, may be temporarily and/or permanently stored in storage device 306. For example, data representative of one or more executable applications 316 (which may include, but are not limited to, one or more of the software applications described herein) configured to direct processor 304 to perform any of the operations described herein may be stored within storage device 306. In some examples, data may be arranged in one or more databases residing within storage device 306.

I/O module 308 may be configured to receive user input and provide user output and may include any hardware, firmware, software, or combination thereof supportive of input and output capabilities. For example, I/O module 308 may include hardware and/or software for capturing user input, including, but not limited to, a keyboard or keypad, a touch screen component (e.g., touch screen display), a receiver (e.g., an RF or infrared receiver), and/or one or more input buttons.

I/O module 308 may include one or more devices for presenting output to a user, including, but not limited to, a graphics engine, a display (e.g., a display screen, one or more output drivers (e.g., display drivers), one or more audio speakers, and one or more audio drivers. In certain embodiments, I/O module 308 is configured to provide graphical data to a display for presentation to a user. The graphical data may be representative of one or more graphical user interfaces ("GUIs"), GUI views, media content views, and/or any other view as may serve a particular application.

In some examples, any of the facilities described herein may be implemented by or within one or more components of computing device 300. For example, one or more applications 316 residing within storage device 306 may be configured to direct processor 304 to perform one or more processes or functions associated with display facility 102, communication facility 104, and/or privacy facility 106. Likewise, storage facility 108 may be implemented by or within storage device 306.

As mentioned, it is often difficult to prevent unauthorized access to patient information displayed on a computer screen or other display device. For example, when a cochlear implant patient is being fitted by an audiologist, a computer screen used by the audiologist to perform the fitting procedure is often visible to the patient. If the audiologist has not yet opened a patient file corresponding to the patient, the patient may be able to see a list of all of the other patients who attend the clinic associated with the audiologist. To this end, the methods and systems described herein prevent unauthorized access to patient information displayed on a display screen that may be accessible to unauthorized users. As will be described herein, such prevention of authorized access may be facilitated by preventing one or more non-search term characters contained within a patient list from being displayed within a graphical user interface until the patient list is narrowed to only include a single entry.

Figure 4:
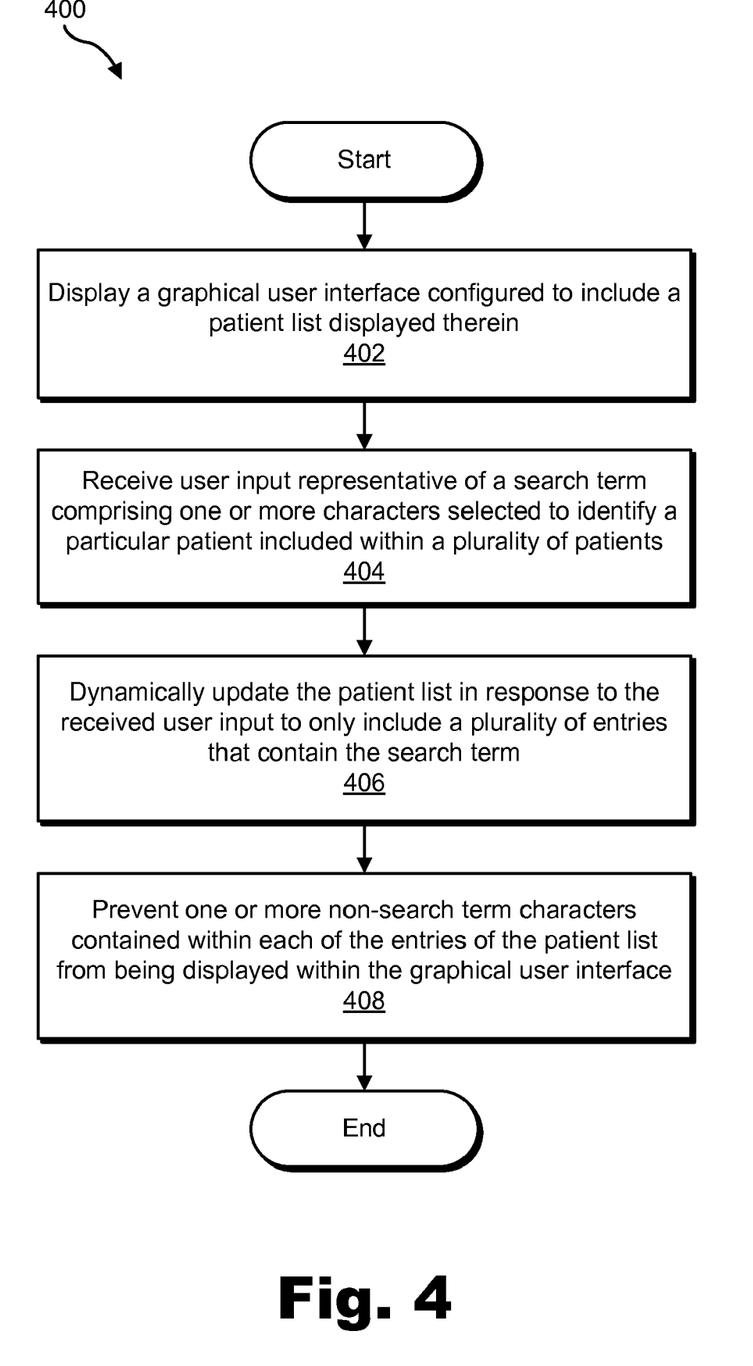
FIG. 4 illustrates an exemplary method of preventing unauthorized access to patient information according to principles described herein.

FIG. 4 illustrates an exemplary method of preventing unauthorized access to patient information. While FIG. 4 illustrates exemplary steps according to one embodiment, other embodiments may omit, add to, reorder, and/or modify any of the steps shown in FIG. 4. One or more of the steps shown in FIG. 4 may be performed by system 100, management subsystem 202 and/or access subsystem 204.

In step 402, a graphical user interface configured to include a patient list displayed therein is displayed. For example, display facility 102, which may include or be implemented on a computing device, may be configured to display a graphical user interface in which patient information corresponding to one or more patients may be displayed. To illustrate, FIG. 5 shows an exemplary GUI 500 that may be displayed on a display screen connected to a personal computer, handheld device, and/or any other computing device as may serve a particular application.

Figure 5:
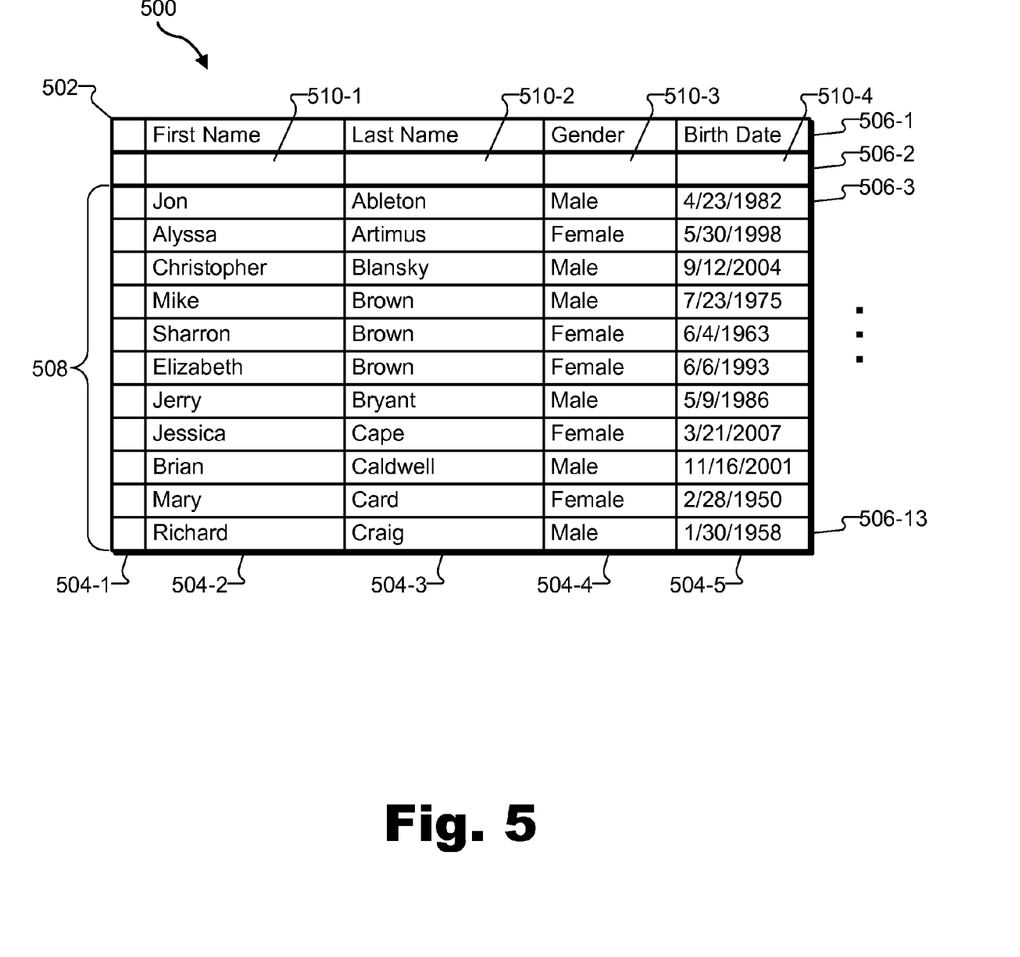
FIG. 5 illustrates an exemplary graphical user interface ("GUI") that may be displayed according to principles described herein.

As shown in FIG. 5, GUI 500 may include a patient information grid 502 configured to display patient information associated with one or more patients of a particular medical facility, doctor, or other medical entity. While a patient information grid 502 is shown in FIG. 5, it will be recognized that other display formats may be used to display patient information corresponding to one or more patients. Patient information grid 502 may include a plurality of columns 504 (e.g., columns 504-1 through 504-5) and a plurality of rows 506 (e.g., rows 506-1 through 506-13). It will be recognized that the patient information grid 502 may include any number of columns 504 and rows 506 as may serve a particular application. In the example of FIG. 5, patient information grid 502 includes a selection column 504-1 configured to facilitate selection of one or more entries displayed within patient information grid 502, a first name column 504-2 configured to display a first name of the patients associated with the entries displayed within patient information grid 502, a last name column 504-3 configured to display a last name of the patients associated with the entries displayed within patient information grid 502, a gender column 504-4 configured to display a gender of each of the patients associated with the entries displayed within patient information grid 502, and a birth date column 504-5 configured to display a birth date of each of the patients associated with the entries displayed within patient information grid 502. Additional or alternative columns may include, but are not limited to, medical identification number columns, social security number columns, and/or any other type of column configured to display patient information therein.

As shown in FIG. 5, patient information grid 502 may include a header row 506-1, a filter row 506-2, and a plurality of patient information rows 506-3. Header row 506-1 may include a name of each of the categories displayed within the various columns 504. For example, header row 506-1 includes headers associated with a first name, a last name, a gender, and a birth date of the patients associated with the entries displayed within patient information grid 502. Filter row 506-2 includes one or more input fields 510 (e.g., input fields 510-1 through 510-4) into which a user may input one or more search terms. Patient information rows 506-3 through 506-13 may be configured to display a patient list 508 that includes one or more entries each corresponding to a distinct patient.

Returning to FIG. 4, in step 404, user input representative of a search term comprising one or more characters selected to identify a particular patient included within a plurality of patients is received. In some examples, communication facility 104 may be configured to receive the user input from a user. For example, medical personnel or other authorized users may enter one or more search terms into filter row 506-2 to narrow or filter patient list 508 until a desired number of entries are included within patient list 508. It will be recognized that filter row 506-2 is merely illustrative of the many different means for receiving a user input search term.

As mentioned, the one or more search terms may be input into one or more of the input fields 510 included within filter row 506-2. For example, if a user desires to access patient information corresponding to a patient with the last name of "Brown," the user may input a search term that includes one or more characters included "Brown" into last name field 510-2. As will be described in more detail below, patient list 508 may be dynamically updated to only include entries containing the user input search term.

In step 406, the patient list is dynamically updated in response to the received user input to only include a plurality of entries that contain the search term received in step 404. For example, privacy facility 106 may be configured to dynamically update patient list 508 displayed in FIG. 5 as each character within a search term is input into one of the input fields 510 of filter row 506-2.

In step 408, one or more non-search term characters contained within each of the entries of the patient list are prevented from being displayed within the graphical user interface. In this manner, as will be described in more detail below, unauthorized access to patient information by a patient or other bystander physically present in the vicinity of the display screen on which the patient list is displayed may be prevented.

Figure 6:
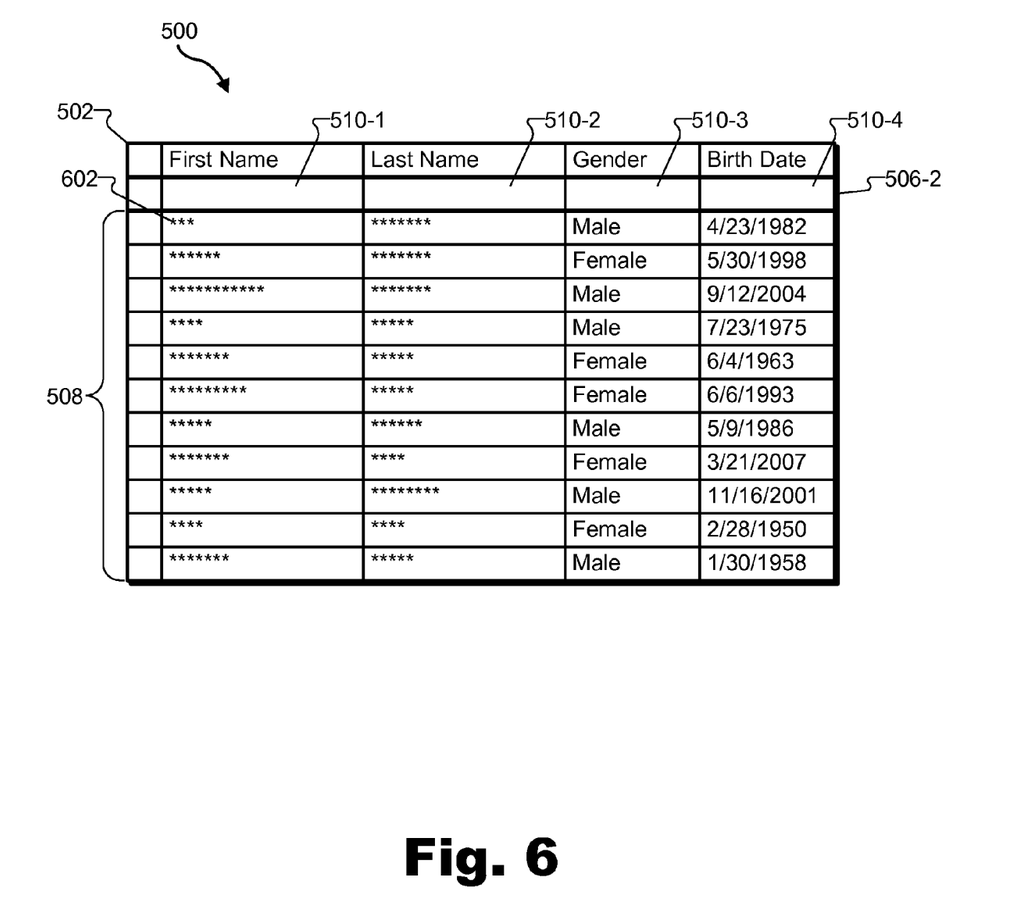
FIG. 6 shows the GUI of FIG. 5 prior to a search term being entered into a filter row.

In some examples, privacy facility 106 may be configured to prevent one or more non-search term characters contained within each of the entries of the patient list from being displayed within the graphical user interface by displaying a password character in place of one or more non-search term characters contained within each of the entries. For example, FIG. 6 shows GUI 500 prior to a search term being entered into filter row 506-2. To prevent patient information from being viewed or otherwise accessed by an unauthorized user, a password character (e.g. password character 602) may be displayed in place of each of the characters included within the first and last names of the patients. While only the first and last names are hidden in this manner in FIG. 6, it will be recognized that any other patient information associated with each of the patients may be hidden in a similar manner. For example, the gender and birth date of each of the patients associated with the entries displayed within patient information grid 502 may be hidden using password characters or in any other manner as may serve a particular application.

Figure 7:
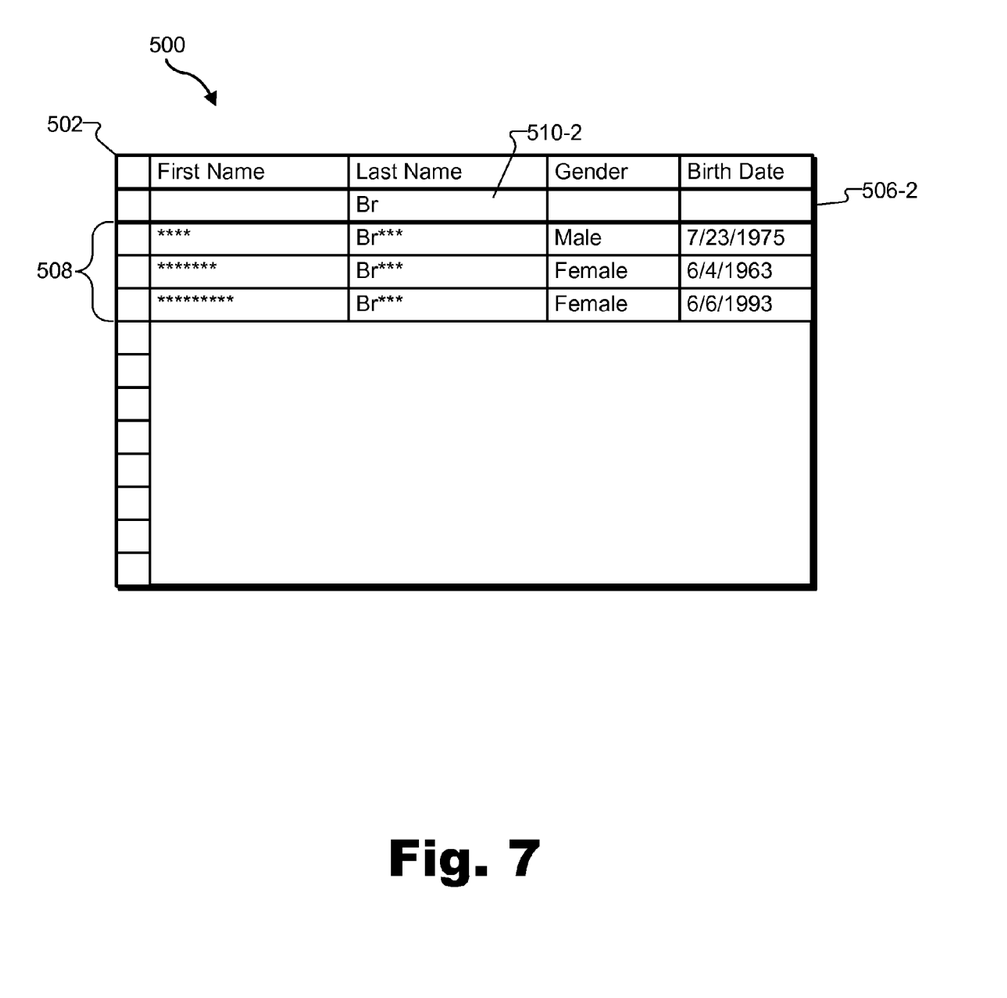
FIG. 7 shows the GUI of FIG. 5 after a user has input a search term into a filter row according to principles described herein.

As a user inputs a search term into one of input fields 510 of filter row 506-2, patient list 508 may be dynamically updated in real-time to include only those entries that contain the search term. For example, FIG. 7 shows GUI 500 after a user has input a search term of "Br" into the last name field 510-2 of filter row 506-2. As shown in FIG. 7, patient list 508 has been dynamically updated or narrowed to include only those entries corresponding to patients that have last names that start with "Br".

As shown in FIG. 7, after the search term "Br" has been entered into the last name field 510-2, the matching characters of the last names displayed in each entry of patient list 508 may be displayed. In this manner, a user may see that the entries contained within patient list 508 contain the search term.

Figure 8:
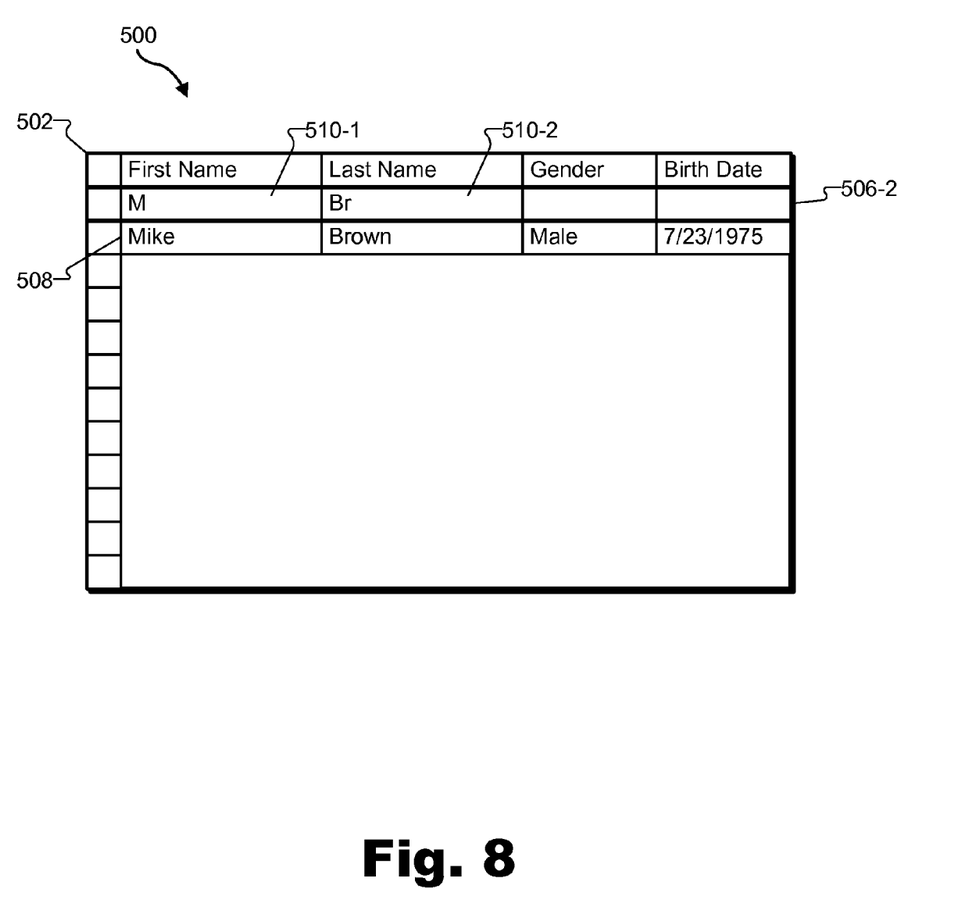
FIG. 8 shows the GUI of FIG. 5 after a user has input another search into a filter row according to principles described herein.

At this point, a user may select one of the entries within the patient list 508 to access additional patient information corresponding to a patient associated with the selected entry. Alternatively, the user may input one or more additional search terms to further narrow patient list 508. For example, FIG. 8 shows GUI 500 after a user has input the search term "M" into the first name field 510-1 of filter row 506-2. As shown in FIG. 8, patient list 508 has been narrowed to include a single entry that includes both the search term "Br" in the last name field and the search term "M" in the first name field. Because patient list 508 only includes a single entry that corresponds to a desired patient, the characters included within the entry do not have to be hidden anymore. Hence, as shown in FIG. 8, the password characters previously displayed have been replaced by the actual characters included within the single entry. In some examples, once the single entry is displayed within patient information grid 502, a user may select the entry in order to access additional patient information corresponding to the patient associated with the entry.

In some alternative embodiments, privacy facility 106 may be configured to prevent one or more non-search term characters contained within each of the entries of the patient list from being displayed within the graphical user interface by preventing the entire patient list from being displayed within the graphical user interface until the patient list has been narrowed to include only a single entry. In this manner, privacy facility 106 may facilitate compliance with relatively more strict privacy policies.

Figure 9:
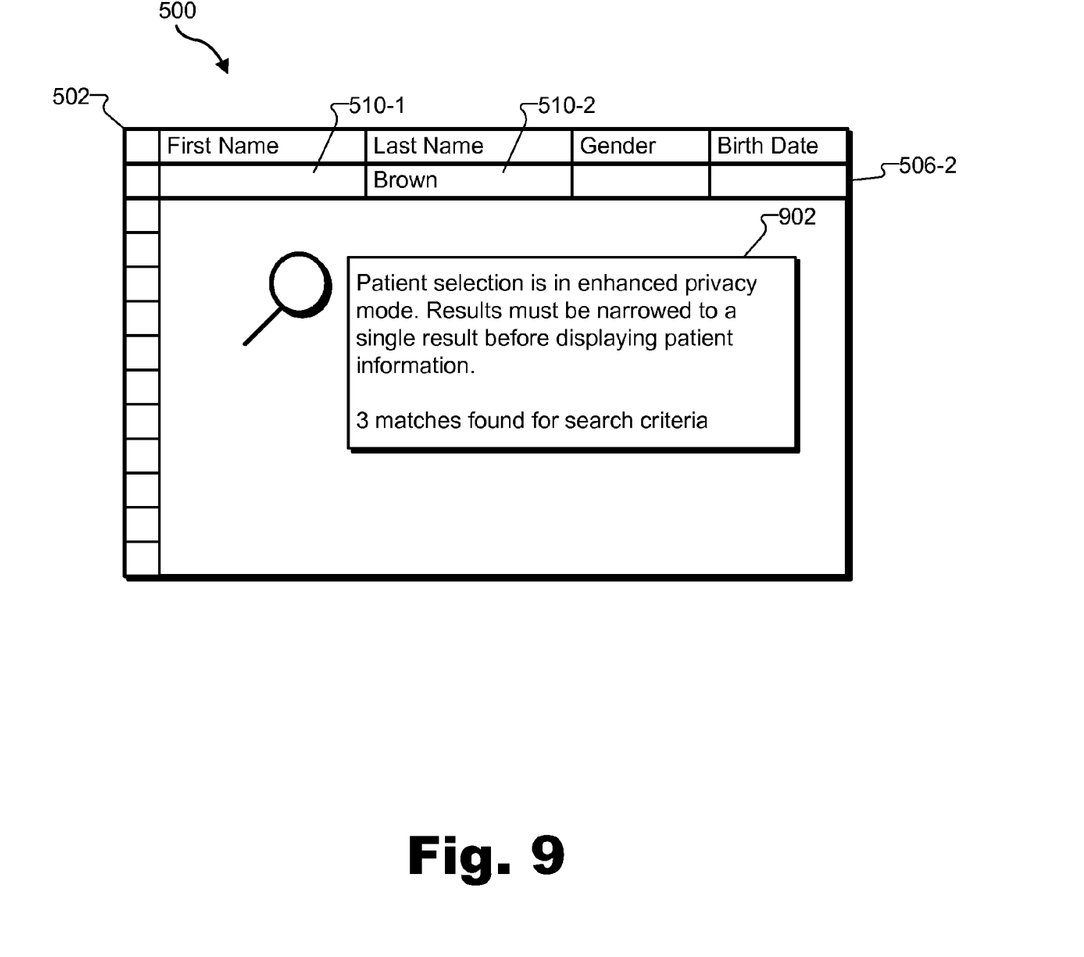
FIG. 9 shows the GUI of FIG. 5 in an enhanced privacy configuration according to principles described herein.

To illustrate, FIG. 9 shows GUI 500 in an enhanced privacy configuration wherein a patient list is prevented from being displayed within GUI 500 until the patient list is narrowed to only include a single entry. As shown in FIG. 9, a text box 902 may be displayed within GUI 500 that explains to the user that the medical software application is operating in the enhanced privacy configuration and that the patient list must be narrowed to a single result before displaying patient information. Text box 902 may further include information corresponding to the number of matches found for the search terms entered into filter row 506-2. For example, FIG. 9 shows that the search term "Brown" has been entered into the last name field 510-2 of filter row 506-2. Text box 902 indicates that 3 entries within a patient list contain a last name of "Brown" and that the patient list must be narrowed to include a single entry before patient information is displayed within GUI 500. In the example of FIG. 9, the patient list may be narrowed by inputting an additional search term of "M" into the first name field 510-1. Once the patient list has been narrowed, GUI 500 may display the single entry in a similar manner to that shown in FIG. 8.

Figure 10:
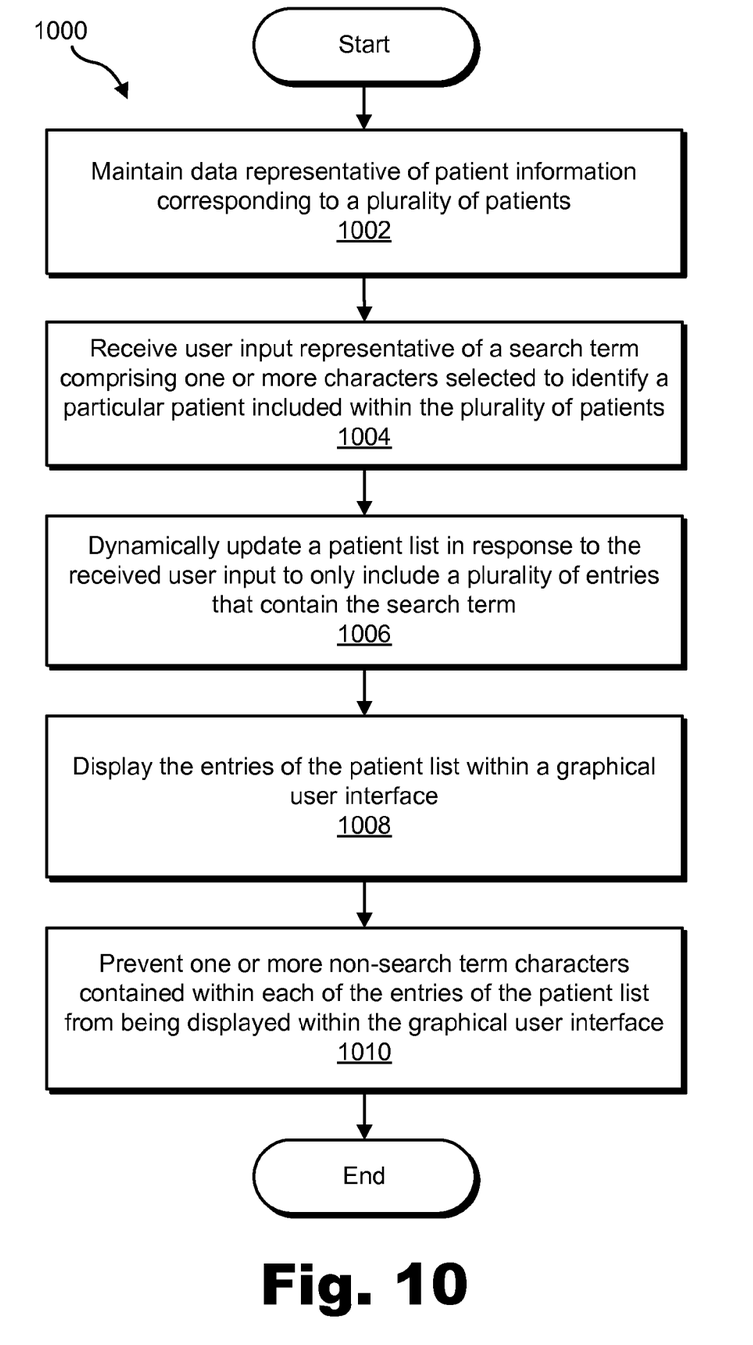
FIG. 10 illustrates another exemplary method of preventing unauthorized access to patient information according to principles described herein.

FIG. 10 illustrates another exemplary method of preventing unauthorized access to patient information. While FIG. 10 illustrates exemplary steps according to one embodiment, other embodiments may omit, add to, reorder, and/or modify any of the steps shown in FIG. 10. One or more of the steps shown in FIG. 10 may be performed by system 100, management subsystem 202 and/or access subsystem 204.

In step 1002, data representative of patient information corresponding to a plurality of patients is maintained. The data may be maintained by storage facility 108, for example.

In step 1004, user input representative of a search term comprising one or more characters selected to identify a particular patient included within the plurality of patients is received. The user input may be received in any of the ways described herein.

In step 1006, a patient list is dynamically updated in response to the received user input to only include a plurality of entries that contain the search term received in step 1004. The patient list may be dynamically updated in any of the ways described herein.

In step 1008, the entries of the patient list are displayed within a graphical user interface. The entries may be displayed in any of the ways described herein. For example, the entries may be displayed within a patient information grid.

In step 1010, one or more non-search term characters contained within each of the entries of the patient list are prevented from being displayed within the graphical user interface. The one or more non-search term characters may be prevented from being displayed in any of the ways described herein.

As detailed above, the methods and systems described herein prevent unauthorized access to patient information. As an example, an exemplary method includes displaying a graphical user interface configured to include a patient list displayed therein, receiving user input representative of a search term comprising one or more characters selected to identify a particular patient included within a plurality of patients, dynamically updating the patient list in response to the received user input to only include a plurality of entries that contain the search term, each of the entries comprising patient information associated with a distinct one of the patients, and preventing one or more non-search term characters contained within each of the entries of the patient list from being displayed within the graphical user interface.

Another exemplary method includes maintaining data representative of patient information corresponding to a plurality of patients, receiving user input representative of a search term comprising one or more characters selected to identify a particular patient included within the plurality of patients, dynamically updating a patient list in response to the received user input to only include a plurality of entries that contain the search term, each of the entries comprising patient information associated with a distinct one of the patients, displaying the entries of the patient list within a graphical user interface, and preventing one or more non-search term characters contained within each of the entries of the patient list from being displayed within the graphical user interface.

An exemplary system includes a display facility, a communication facility, and a privacy facility selectively and communicatively coupled to one another. The display facility is configured to display a patient list within a graphical user interface. The a communication facility is configured to receive user input representative of a search term comprising one or more characters selected to identify a particular patient included within a plurality of patients. The privacy facility is configured to dynamically update the patient list in response to the received user input to only include a plurality of entries that contain the search term, each of the entries comprising patient information associated with a distinct one of the patients, and prevent one or more non-search term characters contained within each of the entries of the patient list from being displayed within the graphical user interface.

In the preceding description, various exemplary embodiments have been described with reference to the accompanying drawings. It will, however, be evident that various modifications and changes may be made thereto, and additional embodiments may be implemented, without departing from the scope of the invention as set forth in the claims that follow. For example, certain features of one embodiment described herein may be combined with or substituted for features of another embodiment described herein. The description and drawings are accordingly to be regarded in an illustrative rather than a restrictive sense.

What is claimed is:
1. A method comprising:
   displaying a graphical user interface configured to include a patient list displayed therein;
   receiving user input representative of a search term comprising one or more characters selected to identify a particular patient included within a plurality of patients;

dynamically updating the patient list in response to the received user input to only include a plurality of entries that contain the search term, each of the entries comprising patient information associated with a distinct one of the patients;

preventing one or more non-search term characters contained within each of the plurality of entries included in the updated patient list from being displayed within the graphical user interface; and displaying the entries included in the updated patient list within the graphical user interface;

wherein the preventing comprises displaying one or more password characters in place of the one or more non-search term characters contained within each of the entries included in the updated patient list.

2. The method of claim 1, further comprising:

receiving additional user input representative of an additional search term comprising one or more characters;

determining that only a single entry within the plurality of entries included in the updated patient list contains both the search term and the additional search term; and displaying the single entry within the graphical user interface.

3. The method of claim 2, further comprising displaying additional patient information associated with the particular patient in response to a user selection of the single entry.

4. The method of claim 1, further comprising:

displaying a patient information grid within the graphical user interface, the patient information grid comprising a plurality of columns and rows; and displaying each of the entries included in the updated patent list within a distinct row of the patient information grid.

5. The method of claim 4, wherein one of the rows within the patient information grid comprises a filter row with one or more input fields, and wherein the receiving of the user input comprises receiving data input into one or more of the input fields.

6. The method of claim 1, wherein the patient information included within each of the entries included in the updated patent list comprises at least a first and a last name of one of the plurality of patients.

7. The method of claim 1, further comprising maintaining the patient information within a storage facility.

8. The method of claim 1, tangibly embodied as computer-executable instructions stored on at least one non-transitory computer-readable medium.

9. A method comprising:

maintaining data representative of patient information corresponding to a plurality of patients;

receiving user input representative of a search term comprising one or more characters selected to identify a particular patient included within the plurality of patients;

dynamically updating a patient list in response to the received user input to only include a plurality of entries that contain the search term, each of the entries comprising patient information associated with a distinct one of the patients;

displaying the entries included in the updated patient list within a graphical user interface; and preventing one or more non-search term characters contained within each of the plurality of entries included in the updated patient list from being displayed within the graphical user interface by displaying one or more password characters in place of the one or more non-search term characters contained within each of the entries included in the updated patient list.

10. The method of claim 9, further comprising:

receiving additional user input representative of an additional search term comprising one or more characters;

determining that only a single entry within the plurality of entries included in the updated patient list contains both the search term and the additional search term; and displaying the single entry within the graphical user interface.

11. The method of claim 9, further comprising:

displaying a patient information grid within the graphical user interface, the patient information grid comprising a plurality of columns and rows; and displaying each of the entries included in the updated patent list within a distinct row of the patient information grid.

12. The method of claim 11, wherein one of the rows within the patient information grid comprises a filter row with one or more input fields, and wherein the receiving of the user input comprises receiving data input into one or more of the input fields.

13. The method of claim 9, wherein the patient information included within each of the entries included in the updated patent list comprises at least a first and a last name of one of the plurality of patients.

14. The method of claim 9, tangibly embodied as computer-executable instructions on at least one non-transitory computer-readable medium.

15. A system comprising:

at least one computing device that comprises:

a processor;

a display facility configured to display a patient list within a graphical user interface;

a communication facility selectively and communicatively coupled to the display facility and configured to receive user input representative of a search term comprising one or more characters selected to identify a particular patient included within a plurality of patients; and a privacy facility selectively and communicatively coupled to the display facility and to the communication facility and configured to:

dynamically update the patient list in response to the received user input to only include a plurality of entries that contain the search term, each of the entries comprising patient information associated with a distinct one of the patients; and prevent one or more non-search term characters contained within each of the plurality of entries included in the updated patient list from being displayed within the graphical user interface, wherein the display facility is further configured to display the entries included in the updated patient list within the graphical user interface, and wherein the privacy facility is configured to prevent the one or more non-search term characters from being displayed within the graphical user interface by directing the display facility to display one or more password characters in place of the one or more non-search term characters contained within each of the entries included in the updated patient list.

16. The system of claim 15, wherein the communication facility is further configured to receive additional user input representative of an additional search term comprising one or more characters and wherein the privacy facility is further configured to:
  determine that only a single entry within the plurality of entries included in the updated patient list contains both the search term and the additional search term; and
  direct the display facility to display the single entry within the graphical user interface.

17. The system of claim 15, wherein the display facility is further configured to display each of the entries included in the updated patent list within a distinct row of a patient information grid.

\* \* \* \* \*